US005698104A

United States Patent [19]
Rhee et al.

[11] Patent Number: 5,698,104
[45] Date of Patent: Dec. 16, 1997

[54] PURIFICATION PROCESS FOR HIRUDIN USING AFFINITY CHROMATOGRAPHY

[75] Inventors: Sang Ki Rhee, Seoul; Bong Hyun Chung, Taejun; Eui Sung Choi, Taejun; Jung Hoon Sohn, Taejun; Deok Joong Youn, Seoul; Myung Kuk Kim, Seoul; Hae Don Lee, Seoul, all of Rep. of Korea

[73] Assignees: Dong Kook Pharmaceutical Co., Ltd.; Korean Institute of Science and Technology, both of Seoul, Rep. of Korea

[21] Appl. No.: 524,311

[22] Filed: Sep. 6, 1995

[30] Foreign Application Priority Data

Sep. 7, 1994 [KR] Rep. of Korea ............... 1994-22499

[51] Int. Cl.$^6$ ................................. B01D 15/08
[52] U.S. Cl. ...................... 210/635; 210/656; 514/21; 530/324; 530/344; 530/413; 530/416; 530/417; 530/855
[58] Field of Search ...................... 210/635, 636, 210/198.2; 530/324, 344, 413, 416, 417, 855; 514/21

[56] References Cited

U.S. PATENT DOCUMENTS

| | | | |
|---|---|---|---|
| 4,551,271 | 11/1985 | Hochuli | 530/417 |
| 4,832,849 | 5/1989 | Cardin | 210/635 |
| 5,034,133 | 7/1991 | Naveh | 210/635 |
| 5,077,388 | 12/1991 | Tang | 530/351 |
| 5,095,092 | 3/1992 | Badziong | 530/324 |
| 5,169,936 | 12/1992 | Staples | 530/350 |
| 5,179,196 | 1/1993 | Johnson | 530/350 |
| 5,304,310 | 4/1994 | Lang | 210/639 |
| 5,372,719 | 12/1994 | Afeyan | 210/502.1 |

OTHER PUBLICATIONS

Markwardt, "Hirudin as an Inhibitor of Thrombin", Meth. Enzymol., vol. 19:924–932, (1970).

Porath et al., "Metal Chelate Affinity Chromatography, A New Approach to Protein Fractionation", Nature, vol. 258:598–599, (1975).

Bagdy et al., "Hirudin", Meth. Enzymol., vol. 45:669–678, (1976).

Markwardt et al., "Pharmacokinetics and Anticoagulant Effect of Hirudin in Man", Thromb Haemostas (Stuttgart), vol. 52(2): 160–163, (1984).

Walsmann et al., "On the Isolation of the Thrombin Inhibitor Hirudin", Thrombosis Research, vol. 40:563–569, (1985).

Mao et al., "Rapid Purification and Revised Amino–Terminal Sequence of Hirudin: A Specific Thrombin Inhibitor of the Bloodsucking Leech", Analytical Biochemistry, vol. 161:514–518, (1987).

Riehl–Bellon et al., "Purification and Biochemical Characterization of Recombinant Hirudin Produced by Saccharomyces Cerevisiae", Biochemistry, vol. 28:2941–2949, (1989).

Fareed et al., "An Objective Perspective on Recombinant Hirudin: A New Anticoagulant and Antithrombotic Agent", Blood Coagulation and Fibrinolysis, vo. 2:135–147, (1991).

Jung–Hoon et al., "Gene Expression and Secretion of the Anticoagulant Hirudin in *Saccharomycess Cerevisiae*," *Journal of Microbiology and Biotechnolgy*, vol. 1(4):266–273, (1991).

Misawa et al., "High Level Expression and Secretion of Biologically Active Leech Hirudin Variant 1 (HVI) by *Escherichia Coli*,"Proceeding of ApBioch. EC., pp. 62–64, (1992).

*Primary Examiner*—Ernest G. Therkorn
*Attorney, Agent, or Firm*—Foley & Lardner

[57] ABSTRACT

Disclosed herein is a process for purifying hirudin from a solution containing hirudin and other substances, characterized in that the process comprises a step of subjecting the solution to a metal ion affinity chromatography wherein copper ion ($Cu^{++}$) is used as a metal ion and a phosphate buffer is used as an eluent.

12 Claims, No Drawings

PURIFICATION PROCESS FOR HIRUDIN USING AFFINITY CHROMATOGRAPHY

BACKGROUND OF THE INVENTION

1. Field of the Invention

The present invention relates to a purification process for hirudin, and more particularly relates to a process for purifying hirudin by using an affinity chromatography.

2. Description of the Prior Art

Hirudin, which is isolated from the leech, *Hirudo medicinalis*, is a thrombin inhibitor and consists of 65–66 amino acids. About 11 variants of hirudin have been known, which are classified into two groups depending on the sequence of N-terminal amino acid: HV1 of which N-terminal amino acid is Val—Val (Bagdy et al., Meth. Enzymol. 45, 669(1976)) and HV2 of which N-terminal amino acid is Ile-Thr (Walsmann & Markwardt, Thromb. Res. 40, 563(1985)). Both of HV1 and HV2 have been used for treatment of thrombosis. Hirudin shows a thrombin inhibition constant ($K_i$) of $10^{-11}$M to $10^{-14}$M, which indicates that hirudin can inhibit blood coagulation at a very low concentration (Mao et al., Anal. Biochem. 161, 514(1987)). In particular, clinic tests proved that hirudin shows no adverse effects such as allergy, immune responses, or circular disfunction (Markwardt et al., Thromb. Haemostas, 52, 160(1984)).

The amount of hirudin which can be obtained from one *Hirudo medicinalis* is as small as 20 μg (Markwardt, Meth., Enzymol., 19, 924, 1970). Therefore, there had been many attempts to produce a large amount of hirudin by culturing genetically engineered microorganisms (For a review, see Fareed el al., Blood coagulation and Fibrinolysis, 2, 135 (1991)).

Riehl-Bellon et al. employs anion exchange chromatography and reverse phase HPLC to purify hirudin produced by gene cloning techniques (Riehl-Bellon et al., Biochem., 28, 2941(1989)). And, Misawa et al. carries out column chromatography on DEAE-Cellulofine, Butyl-Toyopearl, Sephadex G-25 and Q-Sepharose in turn to purify HV2 from a recombinant *E. coli* culture (Misawa et al., Proceeding of ApBioChEC. p. 62 (1992)).

However, these methods had been developed to only detect the production of hirudin in host cells and is not suitable to be applied to quantitative purification of hirudin.

A recombinant protein for medical uses, which is employed in the form of injection formulation, should be highly purified, and the purification is very important in the light of safety of the preparation and of economic aspects.

For the purpose of purifying proteins for medical uses, immune affinity chromatography using an antigen-antibody reaction has been employed. However, immune affinity chromatography has several drawbacks: it is liable to inactivation and expensive. Therefore, its use was restricted to the final step of purification process.

Under these circumstances, the present inventors have made extensive study for the purpose of providing more convenient and inexpensive purification process for hirudin, and, as a result thereof, found that the use of metal ion affinity chromatography, wherein copper ion ($Cu^{++}$) is used as an affinity adsorbent (metal ion) and a phosphate buffer is used as an eluent, made it possible to accomplish said purpose.

SUMMARY OF THE INVENTION

Thus, one object of the present invention is to provide a process for purifying hirudin at a low cost.

Another object of the present invention is to provide a process for purifying hirudin by using a metal ion affinity chromatography wherein copper ion ($Cu^{++}$) is used as an affinity adsorbent (metal ion) and a phosphate buffer is used as an eluent.

Still another object of the present invention is to provide a process for purifying hirudin from a solution containing hirudin and other substances comprising the steps of:

- passing a copper compound solution through a column packed with a ligand to adsorb copper ion ($Cu^{++}$) to the ligand;
- loading the solution containing hirudin and other substances onto the column to bind hirudin to the copper ion; and
- detaching hirudin from the copper ion and eluting hirudin from the column by using a phosphate buffer as an eluent.

The other objects, features and applications of the present invention will be easily apparent to the ordinary person of the art from the following description.

DETAILED DESCRIPTION OF THE INVENTION

Metal ion affinity chromatography, wherein a metal ion is used as an affinity adsorbent, had been for the first time developed to isolate human serum protein in 1975 (Porath et al., Nature, 258, 598(1975)). Porath et al. teaches that certain amino acids having an imidazole structure are bound to a metal ion adsorbed onto a ligand packed within a chromatographic column by virtue of affinity between the amino acid and the metal ion, and then the amino acids are detached from the metal ion by decreasing the affinity between the amino acid and the metal ion by using an eluent. The metal ion may be exemplified by divalent metal ions such as $Cu^{++}$, $Ni^{++}$ and $Zn^{++}$. The metal ion chromatography has advantages, in industrial aspects, that the ligand to which metal ions are adsorbed can be easily prepared and is excellent in its stability, and immobilization matrix (or carrier) can be recycled.

There has been no attempt to apply metal ion affinity chromatography to isolate or purify hirudin. The present inventors for the first time made attempt to apply metal ion affinity chromatography technique to purify hirudin and established optimum operation conditions thereof.

According to the present invention, the purification process using metal ion affinity chromatography comprises the steps of passing a copper compound solution through a column packed with a ligand to adsorb copper ion ($Cu^{++}$) to the ligand; loading a solution containing hirudin to be purified onto the column to bind hirudin to the copper ion; and detaching hirudin from the copper ion and eluting hirudin from the column by using a phosphate buffer as an eluent.

The ligand, which is immobilized onto a immobilization matrix or carrier and to which copper ion as an affinity adsorbent is adsorbed, may be any one which is employed for metal ion affinity chromatography. The examples of the ligand may include, but not limited thereto, iminodiacetic acid (IDA), tris(carboxymethyl) ethylene diamine (TED) or nitrilo-triacetic acid (NTA). Iminodiacetic acid is preferably employed.

As immobilization matrix or carrier, there may be employed an agarose or dextrose gel such as Sepharose (Pharmacia), Sephadex (Pharmacia), Cellufine (Amicon), Toyopearl (Tosoh) and the like.

Immobilization matrix to which ligand is fixed may be prepared by the techniques known to the ordinary skilled person in the art or may be commercially available.

The metal ion employed for the present invention is a divalent ion, and is preferably copper ion ($Cu^{++}$). The copper ion can be adsorbed to the ligand by passing a solution of copper compound to the column packed with the ligand. The copper compound is preferably copper sulfate. Any other divalent metal ion such as zinc or nickel has no affinity to hirudin, and accordingly can not be used for the purification of hirudin.

Hirudin may be detached from the metal ion by using a buffer such as phosphate, imidazole concentration gradient, pH gradient, or chelating agent such as ethylene diamine tetraacetic acid or ethylene glycol tetraacetic acid. In consideration of yield of hirudin, a phosphate buffer, particularly 50–500 mM phosphate, more particularly about up to 100 mM phosphate buffer is advantageously employed. Phosphate buffer may contain up to 20 mM imidazole, because the addition of imidazole makes it easy to decouple of hirudine from copper ion, when the coupling is very strong.

Hirudin which can be purified by using the process of the present invention may include a natural hirudin isolated from *Hirudo medicinalis*, hirudin-containing culture broth which is obtained by culturing yeasts or bacteria having recombinant DNA coding for hirudin, commercially available unpurified (crude) hirudin preparations and the like. Hirudin which may be produced by a recombinant DNA technique may include HV2 hirudin, Lys47-HV2 which is a HV2 hirudin wherein amino acid 47 is substituted with Lys, or HV1 hirudin.

Yeasts or bacteria carrying a recombinant DNA coding for hirudin may be cultured by a common culture technique widely known to the ordinary skilled person in the art to produce hirudin. And, hirudin may be crudely isolated from culture broth of the yeasts or bacteria by using methods known to the ordinary skilled person in the art, for example by centrifuging the culture broth and subjecting the resulting supernatant to ultra centrifugation. Alternatively, the culture broth may be subjected to ion chromatography, or precipitation using ethanol or acetone.

For the present invention, the term "crude solution containing hirudin" as employed in the application means a solution which contains hirudin as well as other substances, and is used as an equivalent of the term "a solution containing hirudin and other substances". The crude solution containing hirudin may include, but not limited thereto, the culture broth as explained in the above, or crude hirudin isolated from the culture broth, commercially available unpurified hirudin preparations and the like.

Hirudin is quantitatively analyzed by Folin method, and the purity is determined by Sohn method (Sohn et al., J. Microbiol. Biotechnol., 1, 266(1991)) wherein high performance liquid chromatography (HPLC; Bechman, Model System Gold) is carried out on C-8 column (4.6 mm×250 mm, Phenomenex) by using 15–30% gradient of acetonitrile-water.

Anti-thrombin titer of hirudin is expressed as antithrombin unit (ATU). Thrombin activity is standardized as NIH-U, and 1 ATU of hirudin activity is defined as the amount of hirudin which completely inhibits the 1 NIH-U of thrombin activity.

Anti-thrombin titer of hirudin may be determined by following the method of Nadine et al. (Nadine et al., Biochem., 28, 2941(1989)).

That is to say, to 50 µl of thrombin reaction solution (0.1M Tris-Cl, pH 8.0, 0.12M NaCl, 0.01% sodium azide, 0.1% bovine serum albumin) is added 0.005, 0.01, 0.015, 0.02, 0.025 or 0.03 ATU of authentic hirudin (Accurate Chem. & Scientific), or purified hirudin prepared in Examples of the present invention, and then 0.03 NIH-U/50 µl of human thrombin (Sigma) is added thereto. Then, 100 µl of 200 µM Chromozym TH (Boehringer Mannheim), a synthetic substrate for thrombin, is added thereto, and the resulting mixture is incubated at 37° C. for 5 minutes, and color development of Chromozym TH at 405 nm was measured by using a microplate reader. By using the measurements at 405 nm for each authentic and purified hirudin, titer of purified hirudin obtained in Examples is calculated.

The present invention will be described in more detail by way of the following non-limiting Examples.

EXAMPLE 1

Yeast *Saccharomyces cerevisiae* KCTC 8519P was cultured in a mixed culture medium (4% yeast extract, 0.5% casamino acid, 1% succinic acid, 0.4% sodium hydroxide, and 4% galactose as a carbon source), at 30° C. for 52 hours. The cultivation was carried out in fed batch culture process wherein galactose was intermittently added to maintain its concentration to 2–4%.

After completion of the cultivation, the culture broth was centrifuged to give a supernatant, which was filtered through a YM3 ultra filter membrane having molecular weight cut off of 3,000 (Amicon). Thus obtained filtrate was called as "crude solution containing hirudin" and used in the subsequent purification process.

EXAMPLE 2

IDA-Sepharose 6B Fast Flow, which is Sepharose gel to which iminodiacetic acid(IDA) is fixed, was purchased from Sigma. IDA-Sepharose 6B was packed in 1.5×30 cm chromatographic column and 20 mM copper sulfate solution was passed through the column.

EXAMPLE 3

1 ml of the crude solution containing hirudin prepared in Example 1 was passed at a flow rate of 1 ml/min through the IDA-Sepharose 6B Fast Flow column prepared in Example 2 to bind hirudin to copper ion, and then the column was washed with 1 mM phosphate buffer (pH 6.2) to remove unbounded proteins other than hirudin. Then, hirudin was eluted by using 100 mM phosphate buffer (pH 6.2). Fractions from No. 38 to 54, which contain hirudin, were collected and subjected to ultrafiltration through a membrane having molecular weight cut off of 3000. The amount of total protein and activity of hirudin contained in the filtrate was 1.75 mg and 4000 ATU/mg, respectively, while they are 120.8 mg and 68.6 ATU/mg, respectively, for the starting crude solution containing hirudin. The yield and purity of hirudin were 85.6% and 90% or more, respectively.

Comparative Examples 1–2

The procedures described in Examples 1 through 3 were carried out, except that 20 mM nickel ion (Comparative Example 1) or zinc ion (Comparative Example 2) solution was employed instead of copper sulfate solution.

There was no change in the amounts of total protein and activities of hirudin contained in the solution before and after passing through the column.

EXAMPLE 4

Unpurified natural hirudin was purchased from Sigma under the catalogue number of H7016 and purified by following the procedure in Example 3.

The amount of total protein and activity of hirudin before passing through the column was 0.08 mg and 1720 ATU/mg, respectively, while, after passing through the column, they are 0.01179 mg and 10500 ATU/mg, respectively. The yield and purity of hirudin were 90% and 97% or more, respectively.

EXAMPLE 5

Unpurified HV1 was purchased from CalBioChem under the catalogue number of 377855 and purified by following the procedure in Example 3. The detachment of hirudin from the copper ion was carried out by using 100 mM phosphate buffer (pH 6.2) containing 20 mM of imidazole.

The amount of total protein and activity of hirudin before passing through the column was 0.93 mg and 215 ATU/mg, respectively, while, after passing through the column, they are 0.215 mg and 890 ATU/mg, respectively. The yield and purity of hirudin were 96% and 90% or more, respectively.

EXAMPLE 6

Recombinant hirudin, Lys 47-HV2 was purchased from Sigma under the catalogue number of H0393 and purified by following the procedure in Example 3.

The amount of total protein and activity of hirudin before passing through the column was 0.01 mg and 9900 ATU/mg, respectively, while, after passing through the column, they are 0.0095 mg and 12000 ATU/mg, respectively. The yield and purity of hirudin were 90% and 99% or more, respectively.

Comparative Example 3

The procedures described in Examples 1 through 3 were carried out, except that pH gradient from 6 through 4 was formed by using sodium acetate buffer (20 mM) containing 1M NaCl to elute hirudin from the column.

The detachment of hirudin from copper ion was incomplete and the yield of hirudin was about 60%.

EXAMPLE 7

The procedures described in Examples 1 through 3 were carried out, except that tris-carboxymethyl ethylenediamine was employed instead of iminodiacetic acid as a ligand. The yield and purity of hirudin were 86.3% and 90% or more, respectively.

This invention may be practiced or embodied in still other ways without departing from the spirit or essential character thereof. The preferred embodiments described herein are therefore illustrative and not restrictive, the scope of the invention being indicated by the appended claims and all variations which come within the meaning of the claims are intended to be embraced therein.

What is claimed is:

1. A process for purifying hirudin from a solution containing hirudin and other substances, wherein the process comprises a step of subjecting the solution to metal ion affinity chromatography, wherein the metal ion is copper ion ($Cu^{++}$) and a phosphate buffer is used as an eluent.

2. The process of claim 1, which comprises the steps of:

loading a solution containing hirudin and other substances onto a column containing bound copper ion ($Cu^{++}$), to bind hirudin to the copper ion; and releasing hirudin from the copper ion and eluting hirudin from the column by using a phosphate buffer as an eluent.

3. The process of claim 2, wherein said hirudin is a natural hirudin, HV1, HV2 or Lys47-HV2.

4. The process of claim 2, wherein said column containing bound copper ion ($Cu^{++}$) is prepared by passing a copper compound solution through a column packed with a ligand to absorb copper ion ($Cu^{++}$) to the ligand.

5. The process of claim 4, wherein said copper compound solution is a copper sulfate solution.

6. The process of claim 4, wherein said ligand is iminodiacetic acid.

7. The process of claim 1, wherein said hirudin is a natural hirudin, HV1, HV2 or Lys47-HV2.

8. The process of claim 1, wherein said copper ion is provided as copper sulfate.

9. The process of claim 1, wherein said phosphate buffer has a concentration of less than 100 mM.

10. The process of claim 2, wherein said phosphate buffer has a concentration of less than 100 mM.

11. The process of claim 10, wherein said phosphate buffer contains up to 20 mM imidazole.

12. The process of claim 9, wherein said phosphate buffer contains up to 20 mM imidazole.

* * * * *